(12) United States Patent
Sharma et al.

(10) Patent No.: US 12,606,851 B2
(45) Date of Patent: *Apr. 21, 2026

(54) PROCESS FOR XYLITOL PRODUCTION

(71) Applicants: Indian Oil Corporation Limited, Mumbai (IN); Department Of Biotechnology, New Delhi (IN)

(72) Inventors: Ajay Kumar Sharma, Faridabad (IN); Manas Ranjan Swain, Faridabad (IN); Ajit Singh, Faridabad (IN); Anshu Shankar Mathur, Faridabad (IN); Ravi Prakash Gupta, Faridabad (IN)

(73) Assignees: Indian Oil Corporation Limited, Mumbai (IN); Department Of Biotechnology, New Delhi (IN)

( * ) Notice: Subject to any disclaimer, the term of this patent is extended or adjusted under 35 U.S.C. 154(b) by 526 days.

This patent is subject to a terminal disclaimer.

(21) Appl. No.: 18/173,924

(22) Filed: Feb. 24, 2023

(65) Prior Publication Data

US 2023/0407348 A1 Dec. 21, 2023

Related U.S. Application Data

(63) Continuation-in-part of application No. 17/394,811, filed on Aug. 5, 2021, now Pat. No. 11,618,907.

(30) Foreign Application Priority Data

Aug. 7, 2020 (IN) .............................. 202021033994

(51) Int. Cl.
C12P 7/10 (2006.01)
C12P 7/18 (2006.01)
(52) U.S. Cl.
CPC ..................................... *C12P 7/18* (2013.01)
(58) Field of Classification Search
CPC ............... C12P 7/10; C12P 7/14; C12P 19/14
See application file for complete search history.

(56) References Cited

U.S. PATENT DOCUMENTS

| | | | |
|---|---|---|---|
| 7,482,144 B2 | 1/2009 | Ojamo et al. | |
| 8,921,082 B2 | 12/2014 | Huang et al. | |
| 9,228,178 B2 | 1/2016 | Abbas et al. | |
| 11,618,907 B2 * | 4/2023 | Sharma | C12P 7/10 |
| | | | 435/158 |
| 2007/0141690 A1 | 6/2007 | Karhumaa et al. | |
| 2015/0218598 A1 | 8/2015 | Petkar et al. | |

FOREIGN PATENT DOCUMENTS

| | | |
|---|---|---|
| CN | 101638673 B | 2/2010 |
| CN | 113881714 A | 1/2022 |
| TW | I706037 B | 3/2020 |

OTHER PUBLICATIONS

Converti, Attilio et al., "Influence of Temperature and pH on Xylitol Production from Xylose by Debaryomyces hansenii", Biotechnology and Bioengineering, Oct. 5, 2001, pp. 39-45, vol. 75, No. 1.

Cortivo, Paulo Roberto Dall et al., "Fermentation of oat and soybean hull hydrolysates into ethanol and xylitol by recombinant industrial strains of *Saccharomyces cerevisiae* under diverse oxygen environments", Industrial Crops & Products, 2018, pp. 10-18, vol. 113.

Dasgupta, Diptarka et al., "Lignocellulosic sugar management for xylitol and ethanol fermentation with multiple cell recycling by Kluyveromyces marxianus IIPE453", Microbiological Research, http://dx.doi.org/10.1016/j.micres.2017.04.002.

Dymtruk, Olena V. et al. "Engineering of xylose reductase and overexpression of xylitol dehydrogenase and kylulokinase improves xylose alcoholic fermentation in the thermotolerant yeast Hansenula polymorpha", Microbial Cell Factories, Jul. 23, 2008, vol. 7:21.

Hallborn, Johan et al., "Xylitol Production by recombinant *Saccharomyces cerevisiae*", Nature Biotechnology, Nov. 1991, pp. 1090-1095, vol. 9.

Hickert, Lilian Raquel et al., "Simultaneous saccharification and co-fermentation of un-detoxified rice hull hydrolysate by *Saccharomyces cerevisiae* ICV D254 and Spathaspora arborariae NRRL Y-48658 for the production of ethanol and xylitol", Bioresource Technology, 2013, pp. 112-116, vol. 143.

Lee, Woo-Jong et al., "Characterization of two-substrate fermentation processes for xylitol production using recombinant *Saccharomyces cere6isiae* containing xylose reductase gene", Process Biochemistry, 2000, pp. 1199-1203, vol. 35.

Meyrial, V. et al., "Xylitol Production From D-Xylose by Candida G Llermondii: Fermentation Behaviour", Biotechnology Letters, Mar. 12, 1991, pp. 281-286, vol. 13, No. 4.

Mishra, A. et al, "Lignocellulosic bioethanol production employing newly isolated inhibitor and thermotolerant *Saccharomyces cerevisiae* DBTIOC S24 strain in SSF and SHF", RSC Advances, 2016, DOI: 10.1039/C6RA00007J.

Sampaio, Fabio C. et al., "Optimal activity and thermostability of xylose reductase from Debaryomyces hansenii UFV-170", J Ind Microbiol Biotechnol, 2009, pp. 293-300, vol. 36.

Swain, Manas R. et al., "Improved conversion of rice straw to ethanol bycombination of moderate temperature ammonia pretreatment andsequential fermentation using Candida tropicalis", Industrial Crops and Products, 2015, pp. 1039-1046, vol. 77.

Zahed, Omid et al., "Continuous co-production of ethanol and xylitol from rice straw hydrolysate in a membrane bioreactor", Folia Microbiol, Sep. 9, 2015, DOI 10.1007/s12223-015-0420-0.

* cited by examiner

*Primary Examiner* — Tekchand Saidha
(74) *Attorney, Agent, or Firm* — Workman Nydegger

(57) ABSTRACT

The present invention relates to a process for production of xylitol. More particularly, the present invention provides an improved process for high titer xylitol production from pure xylose. The process of the present invention results in enhanced xylitol production in shortest duration of time.

10 Claims, 2 Drawing Sheets

Specification includes a Sequence Listing.

Previous xylitol Fermentation by
*S. cerevisiae*

Improved xylitol Fermentation by
*S. cerevisiae*

SEQUENCE LISTING

```
Sequence total quantity: 1
SEQ ID NO: 1           moltype = DNA  length = 644
FEATURE                Location/Qualifiers
source                 1..644
                       mol_type = other DNA
                       organism = synthetic construct
SEQUENCE: 1
ggcttgtaag tttctttctt gctattccaa acggtgagag atttctgtgc ttttgttata  60
ggacaattaa aaccgtttca atacaacaca ctgtggagtt ttcatatctt tgcaactttt  120
tctttgggca ttcgagcaat cggggcccag aggtaacaaa cacaaacaat tttatttatt  180
cattaaattt ttgtcaaaaa caagaatttt cgtaactgga aattttaaaa tattaaaaac  240
tttcaacaac ggatctcttg gttctcgcat cgatgaagaa cgcagcgaaa tgcgatacgt  300
aatgtgaatt gcagaattcc gtgaatcatc gaatctttga acgcacattg cgccccttgg  360
tattccaggg ggcatgcctg tttgagcgtc atttccttct caaacattct gtttggtagt  420
gagtgatact ctttggagtt aacttgaaat tgctggcctt ttcattggat gtttttttc  480
caaagagagg tttctctgcg tgcttgaggt ataatgcaag tacggtcgtt ttaggtttta  540
ccaactgcgg ctaatctttt ttatactgag cgtattggaa cgttatcgat aagaagagag  600
cgtctaggcg aacaatgttc tcaaagtttg acctcaaatc aggt               644
```

PROCESS FOR XYLITOL PRODUCTION

INCORPORATION BY REFERENCE TO A SEQUENCE LISTING

This application includes a Sequence Listing XML submitted electronically in XML format. The Sequence Listing XML, created Jun. 24, 2023, is named "1348US2014.xml," which is 2.49 KB in size. The Sequence Listing XML replaces the content of the XML format of the sequence listing named "Ribosomal DNA Sequence.xml," which is 2.27 KB in size, was created on Dec. 13, 2022, and electronically submitted via patent Center. The Sequence Listing XML herewith is incorporated herein by reference in its entirety.

CROSS-REFERENCE TO RELATED APPLICATIONS

The present patent application is a patent of addition of the main Indian Patent Application No. 202021033994 of Filing date Aug. 7, 2020, and Publication date Feb. 11, 2022. The present application comprises an improvement or a modification of the invention claimed in the specification of the main patent applied in the Indian Patent Application No. 202021033994.

FIELD OF THE INVENTION

The present invention relates to a process for production of xylitol. More particularly, the present invention provides an improved process for high titer xylitol production from pure xylose. The process of the present invention results in xylitol production with near to maximum theoretical yield in shortest duration of time.

BACKGROUND OF THE INVENTION

Xylose is second most abundant sugar found in the lignocellulosic biomass. It possess high sweetening power and 40% less calories compared to sucrose. Xylose has several health benefits such as high solubility, low glycemic rates, lack of carcinogenicity and cariostatic properties. These characteristics confirm the application of xylitol in different food production process such as beverages, candies, chocolates, ice creams several other items. Further, due to several health benefits, xylitol demand is increasing in developing and developed countries significantly. In normal practice at industrial level, xylitol is produced by chemical means through four fundamental stages: (1) obtaining xylose by acid hydrolysis; (2) purification of the hydrolysate; (3) catalytic hydrogenation of xylose; and (4) purification of xylitol. This technology involves high energy consumption, mainly in the stages of hydrogenation and purification. Conversion of xylitol from agrowaste derived xylose by biological root is considered as the cheapest and environment friendly approach. Further, agricultural waste has been widely investigated for the production of xylitol. The agricultural materials undergo pretreatment to expose constitute sugars, so that it can be used later carbon source by different microorganisms. Among many of the pretreatment in biorefinery industry, dilute acid pretreatment is considered as the best practice for the removal of xylose from the lignocellulosic biomass. Due to high severity of the pretreatment condition, several inducers such as furfural, HMF, aliphatic acids and several phenolic compounds are produced which normally limits microbial growth and impact metabolic stress on fermenting microbes. Several species of microorganisms are also able to produce xylitol from xylose, but bacteria and fungi have been studied to a lesser extent compared with that using yeast. A few bacteria such as *Enterobacter liquefaciens* (Yoshitake et al., 1973), *Corynebacterium* sp. (Rangaswamy and Agblevor et al., 2002), *Mycobacterium smegmatis* (Izumori and Tuzaki et al., 1988) and *Gluconobacter oxydans* (Suzuki et al., 2002) have been reported to synthesize xylitol from pure D-xylose. The best xylitol producers among the microorganisms are considered to be yeasts. The screening of different xylose-fermenting yeasts has confirmed that the highest producer of xylitol comes from the genus *Candida* sp. such as *Candida pelliculosa, C. boidinii, C. guilliermondii,* and *C. tropicalis* (Winkelhausen and Kuzmanova et al., 1998; Nigam and Singh et al., 1995). In the microbial process using wild-type xylose-fermenting yeast, xylitol yield obtained from pure xylose is in a range of 65-85% (Nigam and Singh et al., 1995). Among the genetically modified strain, *S. cerevisiae* is studied widely for xylitol production because the yeast strain is considered safe and also widely explored for ethanol production at commercial scale (Kogje and Ghosalkar et al., 2017). However, naturally isolated *S. cerevisiae* is not able to produce xylitol from xylose due to absence of xylose reductase gene (XR) in it. Although *S. cerevisiae* doesn't grow on xylose as the sole carbon source, however this yeast has gene NADPH-dependent aldose reductase (Gre 3) in its genome, which encodes an enzyme that can convert xylose into xylitol-enzyme being expressed under stress induced conditions. Recent studies reveled that Gre 3 over expression in *S. cerevisiae* facilitates xylose fermentation to xylitol (Kogie and Ghosalkar, et al., 2017; Hallborn et al., 1991; Govindan et al., 2001). Further, there are several reports related to xylitol production from genetically modified *S. cerevisiae* and *Candida* sp. and most of the studies include expression of XR or GRE3 gene.

Thierry Lebeau et.al., 1997 relates to the conversion of D-xylose to xylitol by *S. cerevisiae* strain in an aerobic environment by fermenting a mixture of glucose and xylose (7:3 w/v %) and pH at 5.0.

TWI706037B describes a process of xylitol production in which *S. cerevisiae* strain ferments the xylose hydrolysate at a temperature range of 30-35° C. and pH range of 4.0-7.0.

CN101638673B describes a method for manufacturing sugar alcohol by the fermentation of plant straws using *S. cerevisiae*, where fermentation temperature is controlled between 30-36° C., the pH is controlled between 4.4-6.0, stirring speed 150-300 rpm and the fermentation cycle is maintained for 55-75 hours.

Siwaporn Wannawilai et. al., 2017 describes enhancement in xylitol production from xylose by *Candida magnoliae*, when furfural and glucose together supplemented on the fermentation medium.

Biao Zhang et al., 2021 relates to production of xylitol by simultaneous co-utilization of glucose and xylose (1:2 w/v ratio), by engineered Kluveromyces *marxianus* at 37° C. under aerobic conditions.

CN113881714A discloses a process for xylitol production from agricultural and forestry waste biomass by *E. coli*, in which culturing is done at 220-260 rpm for 12-16 hours, followed by aerobic fermentation at 80-100 rpm for 36-48 hours, maintaining the temperature at 36-38° C. and pH at 6.5-7.5 and utilizing 0.2-2.0 w/v % yeast extract.

Although, available literature provides several methods for the production of xylitol, however, the available methods faces several challenges. Thus, there is a need in the art to develop a process which results in enhanced xylitol productivity. The main Indian Patent Application No. 202021033994 described a process wherein *S. cerevisiae* DBT-IOC S24 (MTCC 25086) natural strain was induced to produce xylitol (37 g/L) from xylose (41 g/L) after hours of fermentation at 37° C. (yield of 0.904 g/g) and in presence of inducers (furfural and HMF) using dilute acid pretreated agricultural biomass as well as from xylose containing synthetic media in presence of glucose. In the present invention, an improved process has been disclosed wherein xylitol titer is being increased and process time is further reduced by adopting changes in the incubation temperature and performing fermentation in fed batch mode. Accordingly, the process disclosed in the present invention has several advantages over the main Indian Patent Application No. 202021033994 as described below:

The process disclosed in the present invention results in higher titer (10.9%) of xylitol as compared to the process disclosed in main Indian Patent application.

The process of the present invention results in higher specific productivity of xylitol.

The process of the present invention results in production of xylitol in shortest duration of time i.e., 72 hours.

SUMMARY OF THE INVENTION

In an aspect of the present invention, there is provided an improved process for high titer xylitol production from pure xylose, the process comprising:

(i) inoculating a thermotolerant and inhibitor tolerant yeast strain to a culture medium;

(ii) incubating the strain in the culture medium of step (i) at a temperature of 28° C. at 200 rpm for a duration of 24 hours and increasing the temperature to 37° C.;

(iii) continuously adding glucose and inducer in the medium in pulse feed of every 15 minutes after 6 hours and maintaining aeration at 1VVM and pH at 5; and (iv) obtaining xylitol from the medium.

In an embodiment of the present invention, there is provided an improved process for high titer xylitol production, wherein the thermotolerant and inhibitor tolerant yeast strain is *Saccharomyces cerevisiae* DBT-IOC S24 (MTCC 25086).

In another embodiment of the present invention, there is provided an improved process for high titer xylitol production, wherein the culture medium comprises pure sugars, yeast extract, nutrient broth and inducers.

In yet another embodiment of the present invention, there is provided an improved process for high titer xylitol production, wherein the pure sugars consists of glucose and xylose in a combination ratio of 1:4.

In still embodiment of the present invention, there is provided an improved process for high titer xylitol production, wherein the yeast strain is inoculated to the culture medium at a concentration of 2 g/L cell.

In an embodiment of the present invention, there is provided an improved process for high titer xylitol production, wherein the inducers are selected from 5-Hydroxymethylfurfural (HMF) and furfural.

In another embodiment of the present invention, there is provided an improved process for high titer xylitol production, wherein in step (iii), the glucose and furfural is added in the medium at a rate of 0.2 g/L and 0.8 µM/L, respectively.

In yet another embodiment of the present invention, there is provided an improved process for high titer xylitol production, wherein the process results in 10.9% xylitol in 72 hours of fermentation.

In still another embodiment of the present invention, there is provided an improved process for high titer xylitol production, wherein the process is performed in a fed batch mode.

In an embodiment of the present invention, there is provided an improved process for high titer xylitol production, wherein the concentration of xylose is increased to 6% and concentration of glucose is increased to 1%.

These and other features, aspects, and advantages of the present subject matter will be better understood with reference to the following description. This summary is provided to introduce a selection of concepts in a simplified form.

BRIEF DESCRIPTION OF DRAWINGS

These and other features, aspects, and advantages of the present invention will become better understood when the following detailed description is read with reference to the accompanying drawings in which like characters represent like parts throughout the drawings wherein:

FIG. 1A illustrates optimum xylitol production achieved at 120 hours; and FIG. 1B illustrates optimum xylitol production achieved at 72 hours.

DETAILED DESCRIPTION OF THE INVENTION

Figure 1A:
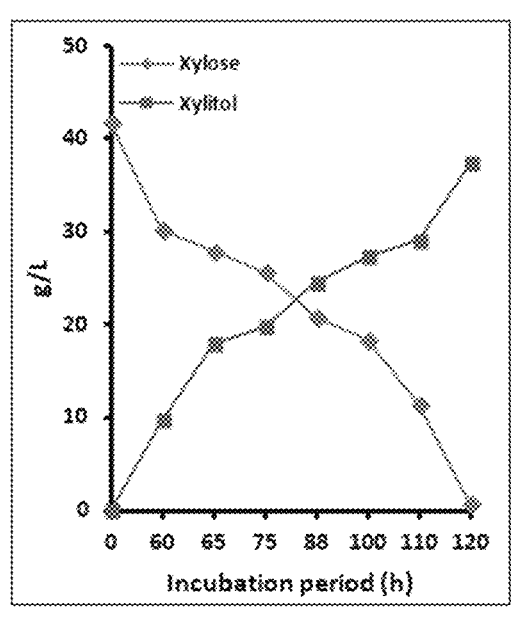
FIGS. 1A and 1B illustrate conversion of xylose to xylitol by *S. cerevisiae*. The xylose to xylitol conversion was achieved in the presence of glucose, inducers (HMF and Furfural) and aeration.
Figure 1A:
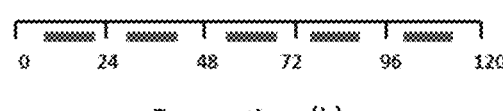
Figure 1B:
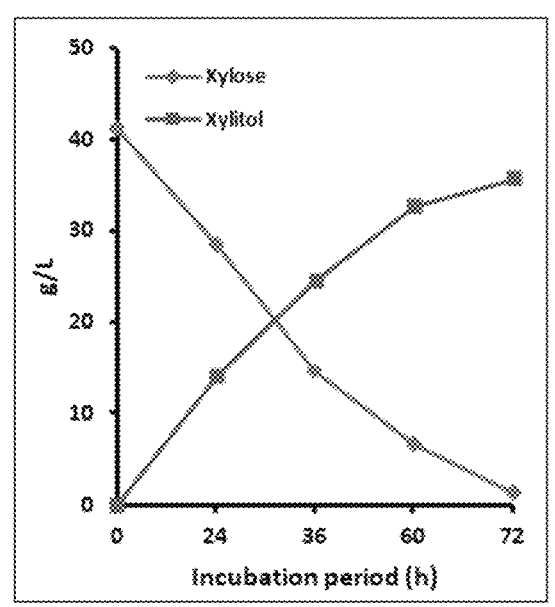
Figure 1B:
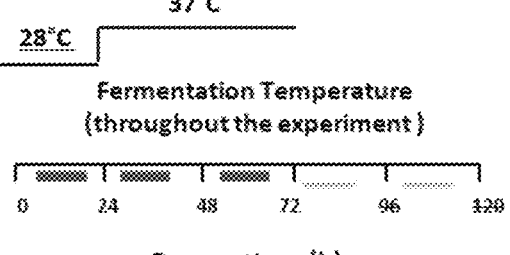

While the invention is susceptible to various modifications and alternative forms, specific embodiment thereof will be described in detail below. It should be understood, however that it is not intended to limit the invention to the particular forms disclosed, but on the contrary, the invention is to cover all modifications, equivalents, and alternative falling within the scope of the invention as defined by the appended claims.

Definition

For the purposes of this invention, the following terms will have the meaning as specified therein:

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

The present invention provides an improved process for xylitol production from pure xylose using *Saccharomyces*

*cerevisiae* DBT-IOC S24 MTCC 25086 (Deposited in IDA MTCC Chandigarh on Mar. 17, 2016 (MTCC Accession No. MTCC 25086). The process of present invention results in high titer xylitol production in shortest duration of time. In this approach of xylitol production, *S. cerevisiae* DBT-IOC S24 is allowed to grow at a temperature of 28° C. for 24 hours and after this temperature of the process is increased to 37° C. which make the xylitol concentration (37 g/L) conversion faster (72 hours) compared to the process described in main Indian Patent Application No. 202021033994. Particularly, in previous study, the *S. cerevisiae* DBT-IOC S24 (MTCC 25086) was induced to produce xylitol (37 g/L) from xylose (41 g/L) after 120 hours of fermentation at 37° C. (yield of 0.904 g/g) at presence of inducers (Furfural and HMF) using dilute acid pretreated agricultural biomass as well as from xylose containing synthetic media in presence of glucose. However, in the present invention, xylitol titer was increased, and process time was further reduced by adopting changes in the incubation temperature and performing the process in fed batch mode.

Thus, in accordance with the present invention, there is provided an improved process for high titer xylitol production from pure xylose, the process comprising:

(i) inoculating a thermotolerant and inhibitor tolerant yeast strain to a culture medium;

(ii) incubating the strain in the culture medium of step (i) at a temperature of 28° C. at 200 rpm for a duration of 24 hours and increasing the temperature to 37° C.;

(iii) continuously adding glucose and inducer in the medium in pulse feed of every 15 minutes after 6 hours and maintaining aeration at 1VVM and pH at 5; and tion, wherein the inducers are selected from 5-Hydroxymethylfurfural (HMF) and furfural.

In another embodiment of the present invention, there is provided an improved process for high titer xylitol production, wherein in step (iii), the glucose and furfural is added in the medium at a rate of 0.2 g/L and 0.8 μM/L, respectively.

In an embodiment of the present invention, there is provided an improved process for high titer xylitol production, wherein the process results in 10.9% xylitol in 72 hours of fermentation.

In another embodiment of the present invention, there is provided an improved process for high titer xylitol production, wherein the process is performed in a fed batch mode.

In an embodiment of the present invention, there is provided an improved process for high titer xylitol production, wherein the concentration of xylose is increased to 6% and concentration of glucose is increased to 1%.

The process of the present invention results in high titer xylitol production from pure xylose using natural *Saccharomyces cerevisiae* DBT-IOC S24 MTCC 25086. Table 1 below indicates xylose to xylitol production by different genetically modified *Saccharomyces cerevisiae* strains as compared to the present invention. The results clearly indicate that process disclosed in the present invention results in high titer xylitol production i.e., 10.9% which make the process more competitive for industrial production. Also, it results in xylitol production in shortest duration of time i.e., within 72 hours of fermentation.

TABLE 1

| Xylose to xylitol production by different genetically modified *Saccharomyces cerevisiae* strains | | | | |
|---|---|---|---|---|
| Name of microorganism | Genetically modification/or not | Xylitol yield (g/g) | Xilitol Titer (g/L) | Reference |
| *Saccharomyces cerevisiae* | Genetically modified | 0.48 | 12.0 | Zha et al., 2014 |
| *Saccharomyces cerevisiae* | Genetically modified | 0.99 | 18.8 | Zha et al., 2013 |
| *Saccharomyces cerevisiae* | Genetically modified | 1.0 | 19.2 | Zha et al., 2013 |
| *Saccharomyces cerevisiae* | Genetically modified | 0.91 | 35.9 | Pratter et al., 2015 |
| *Saccharomyces cerevisiae* | Genetically modified | 0.88 | 24.3 | Baptista et al.,2018 |
| *Saccharomyces cerevisiae* | Natural strain | 0.98 | 109 | Present study |

(iv) obtaining xylitol from the medium.

In an embodiment of the present invention, there is provided an improved process for high titer xylitol production, wherein the thermotolerant and inhibitor tolerant yeast strain is *Saccharomyces cerevisiae* DBT-IOC S24 (MTCC 25086).

In another embodiment of the present invention, there is provided an improved process for high titer xylitol production, wherein the culture medium comprises pure sugars, yeast extract, nutrient broth and inducers.

In an embodiment of the present invention, there is provided an improved process for high titer xylitol production, wherein the pure sugars consists of glucose and xylose in a combination ratio of 1:4.

In another embodiment of the present invention, there is provided an improved process for high titer xylitol production, wherein the yeast strain is inoculated to the culture medium at a concentration of 2 g/L cell.

In an embodiment of the present invention, there is provided an improved process for high titer xylitol produc-

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Improved Process for Xylitol Production Using *S. cerevisiae*

In the present invention, naturally isolated *S. cerevisiae* was used for xylitol production. The strain was isolated from distillery spent wash samples collected in sterile bottles from various sites of three different distilleries from National Capital Region, India. *S. cerevisiae* DBT-IOC S24 (5.8S ribosomal RNA sequence was deposited in IDA: Microbial Type Culture Collection and Gene Bank (MTCC), Chandigarh on Mar. 17, 2016 (Accession no. MTCC 25086). The strain is a moderately thermotolerant and inhibitor tolerant and was inoculated to the culture medium containing pure sugars [glucose (1%) and xylose (4%) in a combination 1:4 ratio], yeast extract (0.2%), nutrient broth (0.1%) along with inducers (HMF or/and furfural) at 10 mM concentration. The yeast was inoculated to the fermentation medium at 2 g/L cell concentration and culture broth was incubated at 28° C. at 200 rpm for 24 hours and after this the temperature of the culture broth was increased to 37° C. Continuous glucose and furfural were being added in pulse feed of every 15 minutes after 6 hours of fermentation at a rate of 0.2 g/L and 0.8 µM/L, respectively. Aeration and pH of the culture medium was maintained to 1VVM and 5.0 respectively throughout the fermentation. Every 24 hours interval the samples were estimated through HPLC for the detection of xylitol (FIG. 1). This experiment was completed after 72 hours of fermentation.

Example 2: Xylitol Production by Fed Batch Mode of Fermentation

Figure 2:
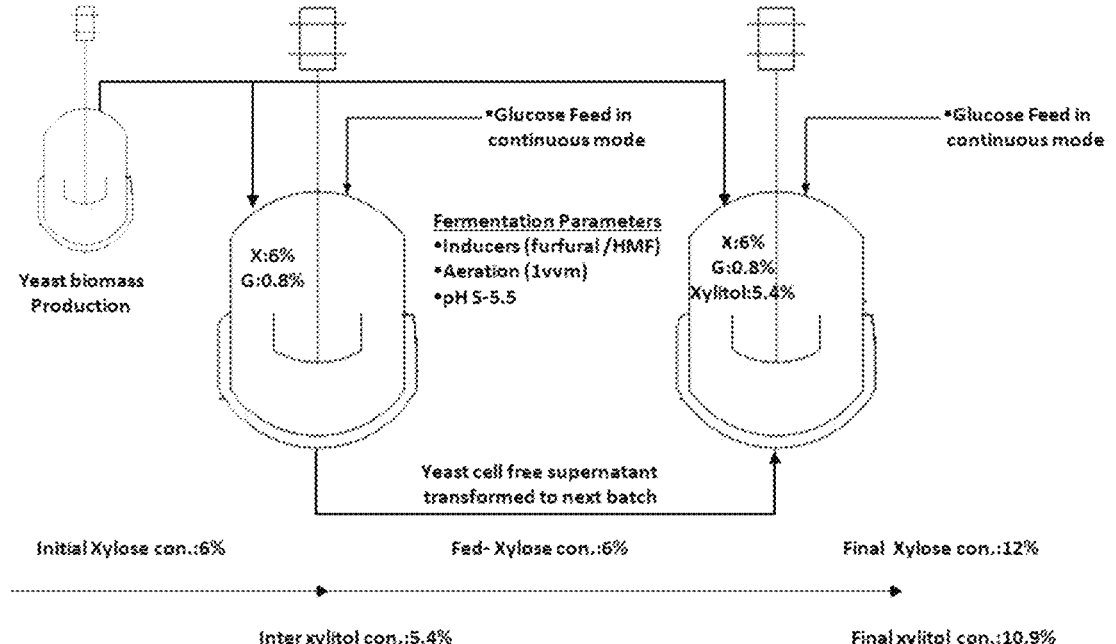
FIG. 2 illustrates high titer xylitol production by fed batch mode. In this approach, xylitol production was achieved from 60 g/L at the first stage of the fermentation after which yeast biomass was separated from the fermentation broth and the second dose of xylose and yeast biomass (4 g/L) was added to the process for further xylitol fermentation.

In another experiment, the xylose concentration in the fermentation broth was increased to 6% along with the glucose concentration of 1% and temperature variation for the process was maintained as described above. After the final xylitol (5.4%) production, the culture broth was allowed to be separated for the yeast cells and the fermentation broth was supplemented by fresh culture yeast and concentrate xylose solution to maintain the final xylose concentration to 6% in the fermentation broth. Continuous glucose and furfural were added in pulse feed of every 15 minutes after 6 hours of fermentation at a rate of 0.2 g/L and 0.8 µM/L, respectively. Aeration and pH of the culture conditions were maintained as described above. After every 24 hours intervals, the samples were collected for the xylose quantification. After 120 hours of the fermentation, 10.9% xylitol concentration was achieved in the fermentation broth. (FIG. 2).

---

---

45

We claim:

1. An improved process for high titer xylitol production from pure xylose, the process comprising:
   i. inoculating a thermotolerant and inhibitor tolerant yeast strain to a culture medium;
   ii. incubating the strain in the culture medium of step (i) at a temperature of 28° C. at 200 rpm for a duration of 24 hours and increasing the temperature to 37° C.;
   iii. continuously adding glucose and inducer in the medium in pulse feed of every after 6 hours and maintaining aeration at 1VVM and pH at 5; and
   iv. obtaining xylitol from the medium.

2. The process as claimed in claim 1, wherein the thermotolerant and inhibitor tolerant yeast strain is *Saccharomyces cerevisiae* DBT-IOC S24 (MTCC 25086).

3. The process as claimed in claim 1, wherein the culture medium comprises pure sugars, yeast extract, nutrient broth and inducers.

4. The process as claimed in claim 3, wherein the pure sugars consists of glucose and xylose in a combination ratio of 1:4.

5. The process as claimed in claim 1, wherein the yeast strain is inoculated to the culture medium at a concentration of 2 g/L cell.

6. The process as claimed in claim 1, wherein the inducers are selected from 5-Hydroxymethylfurfural (HMF) and furfural.

7. The process as claimed in claim 1, wherein in step (iii), the glucose and furfural is added in the medium at a rate of 0.2 g/L and 0.8 µM/L, respectively.

8. The process as claimed in claim 1, wherein the process results in 10.9% xylitol in 72 hours of fermentation.

9. The process as claimed in claim 1, wherein the process is performed in a fed batch mode.

10. The process as claimed in claim 9, wherein the concentration of xylose is increased to 6% and concentration of glucose is increased to 1%.

*     *     *     *     *